US010450237B2

(12) United States Patent
Greenshields et al.

(10) Patent No.: US 10,450,237 B2
(45) Date of Patent: Oct. 22, 2019

(54) MICROBIAL STRAINS, COMPOSITIONS, AND METHODS FOR INCREASING AVAILABLE PHOSPHATE FOR PLANTS

(71) Applicant: NOVOZYMES BIOAG A/S, Bagsvaerd (DK)

(72) Inventors: David Greenshields, Saskatchewan (CA); Shelagh Steckler, Saskatchewan (CA); Kari Priest, Saskatchewan (CA); Caressa Caldwell, Saskatchewan (CA); Michael Frodyma, Roanoke, VA (US)

(73) Assignee: NOVOZYMES BIOAG A/S, Bagsvaerd (DK)

(*) Notice: Subject to any disclaimer, the term of this patent is extended or adjusted under 35 U.S.C. 154(b) by 0 days.

(21) Appl. No.: 15/670,134

(22) Filed: Aug. 7, 2017

(65) Prior Publication Data
US 2017/0334798 A1  Nov. 23, 2017

Related U.S. Application Data

(62) Division of application No. 15/154,278, filed on May 13, 2016, now Pat. No. 9,758,438, which is a division of application No. 14/080,546, filed on Nov. 14, 2013, now Pat. No. 9,365,464.

(60) Provisional application No. 61/727,300, filed on Nov. 16, 2012.

(51) Int. Cl.
| C05F 11/08 | (2006.01) |
| A01N 43/16 | (2006.01) |
| C05G 3/00 | (2006.01) |
| C05B 17/00 | (2006.01) |
| A01H 3/00 | (2006.01) |
| C05B 1/00 | (2006.01) |
| C05B 7/00 | (2006.01) |
| C05F 3/00 | (2006.01) |
| C05F 17/00 | (2006.01) |
| C12R 1/80 | (2006.01) |
| A01N 65/04 | (2009.01) |
| C12N 1/14 | (2006.01) |
| C05G 3/02 | (2006.01) |
| A01N 59/26 | (2006.01) |

(52) U.S. Cl.
CPC ............... *C05F 11/08* (2013.01); *A01H 3/00* (2013.01); *A01N 43/16* (2013.01); *A01N 59/26* (2013.01); *A01N 65/04* (2013.01); *C05B 1/00* (2013.01); *C05B 7/00* (2013.01); *C05B 17/00* (2013.01); *C05F 3/00* (2013.01); *C05F 17/00* (2013.01); *C05G 3/00* (2013.01); *C05G 3/02* (2013.01); *C12N 1/14* (2013.01); *C12R 1/80* (2013.01); *Y02A 40/205* (2018.01); *Y02P 20/145* (2015.11); *Y02W 30/43* (2015.05)

(58) Field of Classification Search
CPC .......... C06F 11/08; C12R 1/80; A01N 43/16; A01N 63/00; C05G 3/00; C05G 3/02; C05B 17/00
USPC ..................................................... 504/117, 11
See application file for complete search history.

(56) References Cited

U.S. PATENT DOCUMENTS

| 5,026,417 | A | 6/1991 | Kucey |
| 5,484,464 | A | 1/1996 | Gleddie |
| 5,503,652 | A | 4/1996 | Kloepper |
| 5,586,411 | A | 12/1996 | Gleddie |
| 5,770,787 | A | 6/1998 | Montague |
| 5,912,398 | A | 6/1999 | Goldstein |
| 6,311,426 | B1 | 11/2001 | Mehta |
| 7,262,151 | B2 | 8/2007 | Smith |
| 8,278,247 | B2 | 10/2012 | Hnatowich |
| 8,357,631 | B2 * | 1/2013 | Smith ............ A01N 43/16 504/117 |
| 8,946,119 | B2 * | 2/2015 | Smith ............ A01N 63/02 504/100 |
| 2004/0261578 | A1 | 12/2004 | Harman |
| 2007/0131009 | A1 | 6/2007 | Westbrook |
| 2010/0099560 | A1 | 4/2010 | Hnatowich |

FOREIGN PATENT DOCUMENTS

| AU | 59111/94 | 6/1994 |
| CN | 1252247 | 4/2006 |
| CN | 1524949 C | 4/2006 |
| CN | 102174412 B | 12/2012 |
| EP | 0284236 A2 | 9/1988 |
| RU | 2192403 C2 | 11/2002 |
| WO | 95/06623 A1 | 3/1995 |
| WO | 95/08521 A1 | 3/1995 |
| WO | 04/035508 A1 | 4/2004 |
| WO | 2008/085958 A1 | 7/2008 |
| WO | 2009/91557 A1 | 7/2009 |
| WO | 2010/037167 A2 | 4/2010 |

(Continued)

OTHER PUBLICATIONS

Elliot et al. Phosphorus Fertilizers for Organic Farming Systems; Colorado State University, Fact Sheet No. 0.569, pp. 1-3. (Year: 2007).*

(Continued)

*Primary Examiner* — Sharmila G Landau
*Assistant Examiner* — Paul C Martin
(74) *Attorney, Agent, or Firm* — Adam Rucker

(57) ABSTRACT

The present invention relates to a novel phosphate solubilizing strain of *Penicillium bilaiae*, which is a hybrid of *Penicillium bilaiae* ATCC 22348 and *Penicillium bilaiae* V08/021001, as well as compositions and methods for using the novel phosphate solubilizing strain to increase the availability of phosphorous for plant uptake from soil.

11 Claims, No Drawings

(56) References Cited

FOREIGN PATENT DOCUMENTS

| WO | 2010/037228 A1 | 4/2010 |
|---|---|---|
| WO | 2011/114280 A2 | 9/2011 |
| WO | 2012/037352 A2 | 3/2012 |

OTHER PUBLICATIONS

Sheehan et al. Spore Germination and Microcycle Conidiation of Two Penicillia in Soil. 76: (3) 523-527 (1984).
Legget et al., First International Meeting on Microbial Phosphate Solubilization, 215-222 (2007).
Legget and Gleddie, Philom. Bios Inc., 318-311 (1995).
Kucey "Phosphate-Solubilizing Bacteria and fungi in Various Cultivated and Virgin Alberta Soils", Can. J. Soil Sci., vol. 63, pp. 671-678 (1983).
Kucey, "Increased Phosphorus Uptake by Wheat and Field Beans Inoculated with a Phosphorus-Solubilizing Penicillium bilaji Strain and with Vesicular-Arbuscular Mycorrhizal Fungi", Applied and Environmental Microbiology, vol. 53, No. 12, pp. 2699-2703 (1987).
Wakelin et al., "The Effect of Penicillium fungi on Plant Growth and Phosphorus Mobilization in Neutral to Alkaline Soils from Southern Australia", Can. J. Microbiol., vol. 53, pp. 106-115 (2007).
Asea et al., "Inorganic Phosphate Solubilization by Two Penicillium Species in Solution Culture and Soil", Soil Bid. Biochem. vol. 20, No. 4, pp. 459-464 (1988).
Barroso and Nahas, "The status of soil phosphate fractions and the ability of fungi to dissolve hardly soluble phosphates", Applied Soil Ecology, vol. 29, pp. 73-83 (2005).
Kucey, "Effect of Penicillium Bilaji on the Solubility and Uptake of P and Micronutrients From Soil by Wheat", Can. J. Soil .Sel, vol. 68, pp. 261-270 (1988).
Pandey et al., "Phosphate solubilization by *Penicillium* spp. isolated from soil samples of Indian Himalayan region", World J Microbiol Biotechnol, vol. 24, pp. 97-102 (2008).
Tulloch et al., Horticultural Science, vol. 27, No. 6, pp. 846 (PS16) (1992).
Pradhan et al., 2005, Afri J Biotech 5(10), 850-854.
Elliott et al, 2007—Fact Sheet 0.569.
Hayat et al, 2010, Microbiol 60(5), 579-598.
Backie et al, 1998, Canadian J of plant science, 78(1), 91-102.
Chai et al, 2011, J Basic Microbiol, 51(1), 5-14.
Khan et al, 2009, Archives of agronomy and foil science, 56(1), 73-98.
Kucey et al, 1989, Can. J. Soil Sci., 692, 425-432.
Richardson et al, 2009, Plant soil, 321(1-2), 305-339.
Kim et al, 2005, J Biosci Bioeng,vol. 99, No. 1, pp. 23-29.
Reyes et al, 1999, FEMS Microbiol Ecol, vol. 28, No. 3, pp. 281-290.
Reyes et al, 2001, Soil Biol Biochem, vol. 33, No. 12-13, pp. 1741-1747.

\* cited by examiner

MICROBIAL STRAINS, COMPOSITIONS, AND METHODS FOR INCREASING AVAILABLE PHOSPHATE FOR PLANTS

CROSS-REFERENCE TO RELATED APPLICATIONS

This application is a divisional of U.S. patent application Ser. No. 15/154,278, filed May 13, 2016, and issued as U.S. Pat. No. 9,758,438, which is a divisional of U.S. patent application Ser. No. 14/080,546, filed Nov. 14, 2013, and issued as U.S. Pat. No. 9,365,464, which claims priority or the benefit under 35 U.S.C. 119 of U.S. Provisional Patent Application No. 61/727,300, filed Nov. 16, 2012, the contents of which are fully incorporated herein by reference.

FIELD OF THE INVENTION

Disclosed herein are novel microbial strains. Compositions comprising the novel microbial strains and methods of using the novel microbial strains are further disclosed, particularly compositions and methods to increase available phosphate for plants.

BACKGROUND OF THE INVENTIONS

In order to maintain healthy growth, plants must extract a variety of elements from the soil in which they grow. These elements include phosphorus and the so-called micro-nutrients (e.g., copper, iron, zinc, etc.), but many soils are deficient in such elements or they contain them only in forms which cannot be readily taken up by plants (it is generally believed that essential elements cannot be readily taken up by plants unless they are present in dissolved form in the soil).

To counteract such deficiencies, sources of the deficient elements are commonly applied to soils in order to improve growth rates and yields obtained from crop plants. For example, phosphates are often added to soil to counteract a lack of available phosphorus. Phosphate added to the soil as a commercial fertilizer (e.g., mono-ammonium phosphate, triple-super-phosphate, etc.) is readily plant available, but is rapidly converted in soil to relatively unavailable forms. It has been estimated that only 10 to 30% of phosphate fertilizer is used by the plant in the year it is applied, and one-third to one-half of the phosphate fertilizer applied may never be recovered by the plant.

Attempts have been made in the past to use microorganisms to improve the availability of essential elements in soil systems. In particular species of the fungus *Penicillium* has been used for this purpose.

For example, U.S. Pat. No. 5,026,417 discloses isolated strains of *P. bilaii* which are capable of improving the uptake of phosphorus by plants when applied to the soil.

U.S. Pat. App. Pub. No.: 2010/0099560 discloses method of enhancing growth conditions for plants by growing the plants in soil containing, in proximity to the plant roots, both a phosphorus source and at least two strains of the fungus *Penicillium*.

U.S. Pat. No. 5,484,464 Methods and compositions for increasing the availability of soluble phosphate and fixed nitrogen for legume: *Rhizobium* symbioses involving co-inoculating legume seeds with a phosphate-solubilizing soil fungus, *Penicillium bilaii*, and *Rhizobium* spp. prior to planting.

There is, however, still a need for systems for improving growth conditions for plants, particularly by increasing the levels of available phosphorus in soil systems.

SUMMARY OF THE INVENTIONS

Described herein are novel fungal strains which solubilize phosphorus. The inventors have isolated and tested a significant number of fungal strains for their ability to solubilize phosphorus.

As disclosed throughout, the isolated strains are strains of the genus *Penicillium* spp. In particular, the isolated strains are strains of *Penicillium bilaiae*. Even more particularly, the isolated strains are isolated *Penicillium bilaiae* strains selected from the group consisting of
   the strain having the deposit accession number NRRL B-50776,
   the strain having the deposit accession number NRRL B-50777,
   the strain having the deposit accession number NRRL B-50778,
   the strain having the deposit accession number NRRL B-50779,
   the strain having the deposit accession number NRRL B-50780,
   the strain having the deposit accession number NRRL B-50781,
   the strain having the deposit accession number NRRL B-50782,
   the strain having the deposit accession number NRRL B-50783,
   the strain having the deposit accession number NRRL B-50784,
   the strain having the deposit accession number NRRL B-50785,
   the strain having the deposit accession number NRRL B-50786,
   the strain having the deposit accession number NRRL B-50787,
   the strain having the deposit accession number NRRL B-50788, and
   a mixture of two or more of the strains thereof.

Also described herein are compositions comprising a carrier and one or more of the fungal strains described herein. The compositions may further comprise a phosphorus source, such as rock phosphate or a phosphorus containing fertilizer, for phosphorus solubilization by the fungal strains of the compositions. The phosphorus source or phosphorus containing fertilizers may be used as part of the same composition or through a separate treatment process.

In another embodiment, the composition comprises one or more plant signal molecules. In one embodiment, the composition comprises at least one lipo-chitooligosaccharide (LCO). In another embodiment the composition comprises at least one chitooligosaccharide (CO). In still another embodiment, the composition comprises at least one flavonoid. In still yet another embodiment, the composition comprises jasmonic acid or a derivative thereof. In another embodiment, the composition comprises linoleic acid or a derivative thereof. In yet another embodiment, the composition comprises linolenic acid or a derivative thereof. In still yet another embodiment, the composition comprises a karrikin.

Further described herein is a method for increasing the availability of phosphorus for plant uptake from soil. The method comprises introducing into the soil an inoculum of one or more of the fungal strains described herein. In another embodiment, the method may further comprise adding a source of phosphorus to the soil. In still another embodiment, the method comprises introducing into the soil an inoculum of one or more of the fungal strains as a seed coating.

Also described herein is a method for increasing the phosphorus uptake in a plant(s) comprising growing a plant(s) in a soil that contains a phosphorus source and one or more of the fungal strains described herein. In one embodiment, the plant(s) is a leguminous plant(s), non-leguminous plant(s), or combinations thereof. In another embodiment, the plant is a plant selected from the group consisting of soybean, bean, alfalfa, clover, corn, lettuce tomatoes, potatoes, cucumbers, and combinations thereof.

Further described herein are seeds coated with the fungal strains described herein.

DETAILED DESCRIPTION OF THE INVENTION

The disclosed fungal strains have been isolated and tested for their ability to solubilize phosphorus. This is described in detail in the "Examples" section provided below. The disclosed embodiments further relate to compositions, seed coatings, methods for increasing the availability of phosphorus for plant uptake from soil, and methods for increasing the phosphorus uptake in plants comprising growing the plants in a soil containing a phosphorus source.

Definitions

As used herein, the singular forms "a", "an" and "the" are intended to include the plural forms as well, unless the context clearly indicates otherwise.

As used herein, the term "biologically pure culture" is intended to mean a culture essentially free from biological contamination and having a genetic uniformity such that different subcultures taken therefrom will display substantially identical genotypes and phenotypes (e.g., cultures have a purity of at least 60%, of at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, up to 100% pure).

As used herein, the term "isolate, isolates, isolating, and/or isolated, etc." is intended to mean that the referenced material is removed from the environment in which it is normally found.

As used herein, the term "inoculum" is intended to mean any form of fungus cells, mycelium, or spores, which is capable of propagating on or in the soil when the conditions of temperature, moisture, etc., are favorable for fungal growth.

As used herein, the terms "spore" has its normal meaning which is well known and understood by those of skill in the art and generally refers to a microorganism in its dormant, protected state.

As used herein, the term "source" of a particular element is intended to mean a compound of that element which, at least in the soil conditions under consideration, does not make the element fully available for plant uptake.

As used herein, the terms "effective amount", "effective concentration", or "effective dosage" is intended to mean the amount, concentration, or dosage of the one or more fungal isolates sufficient to cause the solubilization of a phosphorus source. The actual effective dosage in absolute value depends on factors including, but not limited to, the size (e.g., the area, the total acreage, etc.) of the land for application with the fungal isolates, synergistic or antagonistic interactions between the other active or inert ingredients which may increase or reduce the phosphate solubilizing activity of the fungal isolates, and the stability of the fungal isolates in compositions and/or as seed treatments. The "effective amount", "effective concentration", or "effective dosage" of the fungal pesticide may be determined, e.g., by a routine dose response experiment.

As used herein, the term "carrier" is intended to refer to a medium capable of supporting one or more of the fungal isolates as described herein.

As used herein, the term "soil-compatible carrier" is intended to refer to any material which can be added to a soil without causing/having an adverse effect on plant growth, soil structure, soil drainage, or the like.

As used herein, "at least one biologically active ingredient" is intended to mean biologically active ingredients (e.g., signal molecules, other microorganisms, etc.) other than the one or more fungal isolates described herein.

As used herein the terms "signal molecule(s)" or "plant signal molecule(s)", which may be used interchangeably with "plant growth-enhancing agent(s)," broadly refers to any agent, both naturally occurring in plants or microbes, and synthetic (and which may be non-naturally occurring) that directly or indirectly activates or inactivates a plant biochemical pathway, resulting in increased or enhanced plant growth, compared to untreated plants or plants harvested from untreated seed.

As used herein, terms "increased plant growth" or "enhanced plant growth" are intended to refer to increased plant yield (e.g., increased biomass, increased fruit number, or a combination thereof as measured by bushels per acre), increased root number, increased root mass, increased root volume, increased leaf area, increased plant stand, increased plant vigor, or combinations thereof.

As used herein, the terms "plant(s)" and "plant part(s)" are intended to refer to all plants and plant populations such as desired and undesired wild plants or crop plants (including naturally occurring crop plants). Crop plants can be plants, which can be obtained by conventional plant breeding and optimization methods or by biotechnological and genetic engineering methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material and vegetative and generative propagation material (e.g., cuttings, tubers, rhizomes, off-shoots and seeds, etc.).

As used herein, terms "phosphate solubilization", or "phosphate solubilizing", etc. are intended to mean the conversion of insoluble phosphate (e.g., rock phosphate, etc.) into a soluble phosphate form.

As used herein, the term "phosphate solubilizing organism" is intended to refer to any organism capable of converting insoluble phosphate into a soluble phosphate form.

As used herein, the term "micronutrient(s)" is intended to refer to nutrients which are needed for plant growth, plant health, and/or plant development.

As used herein, the term "biostimulant(s)" is intended to refer to any substance capable of enhancing metabolic or physiological processes within plants and soils.

As used herein, the term "wetting agent(s)" is intended to refer to any substance capable of lowering and/or reducing the surface tension of water.

Strains

In one embodiment, the strain(s) described herein is a phosphate solubilizing fungal strain(s). In another embodiment, the strain(s) is a *Penicillium bilaiae* strain(s). As used herein, the species name "*Penicillium bilaiae*" is intended to include all iterations of the species name "*Penicillium bilaiae*" such as those species names published throughout the literature (e.g., "*Penicillium bilajl*", "*Penicillium bilaiI*", etc.).

In another embodiment, the strain(s) is the progeny of the *Penicillium bilaiae* strain having the deposit accession number V08/021001 (deposited with the National Measurement Institute). In another embodiment, the strain(s) is the progeny of the *Penicillium bilaiae* strain having the deposit accession number ATCC-20851 (deposited with the American Type Culture Collection). In another embodiment, the strain(s) is the progeny of the *Penicillium bilaiae* strain having the deposit accession number ATCC-22348 (deposited with the American Type Culture Collection). In still another embodiment, the strain(s) is the progeny of the *Penicillium bilaiae* strain having the deposit accession number V08/021001 and the *Penicillium bilaiae* strain having the deposit accession number ATCC-20851. In still another embodiment, the strain(s) is the progeny of the *Penicillium bilaiae* strain having the deposit accession number V08/021001 and the *Penicillium bilaiae* strain having the deposit accession number ATCC-22348. In still another embodiment, the strain(s) is the progeny of the *Penicillium bilaiae* strain having the deposit accession number ATCC-20851 and the *Penicillium bilaiae* strain having the deposit accession number ATCC-22348.

In still another embodiment, the strains are *Penicillium* strains selected from the group consisting of:
- the strain having the deposit accession number NRRL B-50776,
- the strain having the deposit accession number NRRL B-50777,
- the strain having the deposit accession number NRRL B-50778,
- the strain having the deposit accession number NRRL B-50779,
- the strain having the deposit accession number NRRL B-50780,
- the strain having the deposit accession number NRRL B-50781,
- the strain having the deposit accession number NRRL B-50782,
- the strain having the deposit accession number NRRL B-50783,
- the strain having the deposit accession number NRRL B-50784,
- the strain having the deposit accession number NRRL B-50785,
- the strain having the deposit accession number NRRL B-50786,
- the strain having the deposit accession number NRRL B-50787,
- the strain having the deposit accession number NRRL B-50788, and
- a mixture of two or more of the strains thereof.

In a particular embodiment, the strain(s) may be one or more of the above mentioned deposited strains (e.g., including at least two of the above strains, at least three of the above strains, at least four of the above strains, at least five of the above strains, at least six of the above strains, at least seven of the above strains, at least eight of the above strains, at least nine of the above strains, at least ten of the above strains, at least eleven of the above strains, at least twelve of the above strains, up to and including all of the above strains).

In an embodiment, the strain is the strain having the deposit accession NRRL B-50776. In an embodiment, the strain is the strain having the deposit accession number NRRL B-50777. In an embodiment, the strain is the strain having the deposit accession number NRRL B-50778. In an embodiment, the strain is the strain having the deposit accession number NRRL B-50779. In an embodiment, the strain is the strain having the deposit accession number NRRL B-50780. In an embodiment, the strain is the strain having the deposit accession number NRRL B-50781. In an embodiment, the strain is the strain having the deposit accession number NRRL B-50782. In an embodiment, the strain is the strain having the deposit accession number NRRL B-50783. In an embodiment, the strain is the strain having the deposit accession number NRRL B-50784. In an embodiment, the strain is the strain having the deposit accession number NRRL B-50785. In an embodiment, the strain is the strain having the deposit accession number NRRL B-50786. In an embodiment, the strain is the strain having the deposit accession number NRRL B-50787. In an embodiment, the strain is the strain having the deposit accession number NRRL B-50788.

In another embodiment, the strain(s) may be a progeny of one of the deposited strains. In another embodiment, the deposited strain(s) is a biologically pure culture (e.g., cultures having a purity of at least 60%, of at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, up to 100% pure).

The deposited fungal cultures are derived from isolated naturally occurring fungal strains. All of the deposited strains were collected in Saskatoon, Canada in 2012. Cultures of the deposited strains may consist of dormant fungal spores and/or viable fungi.

The *Penicillium* fungus described herein, and in particular, the strains having deposit accession numbers NRRL B-50776, NRRL B-50777, NRRL B-50778, NRRL B-50779, NRRL B-50780, NRRL B-50781, NRRL B-50782, NRRL B-50783, NRRL B-50784, NRRL B-50785, NRRL B-50786, NRRL B-50787 and NRRL B-50788, can be grown using solid state or liquid fermentation and a suitable carbon source. *Penicillium* isolates may be grown using any suitable method known to the person skilled in the art. For example, the fungus may be cultured on a solid growth medium such as potato dextrose agar or malt extract agar, or in flasks containing suitable liquid media such as Czapek-Dox medium or potato dextrose broth. These culture methods may be used in the preparation of an inoculum of *Penicillium* spp. for coating seeds and/or application to carrier to be applied to soil.

Solid state production of *Penicillium* spores may be achieved by inoculating a solid medium such as a peat or vermiculite-based substrate, or grains including, but not limited to, oats, wheat, barley, or rice. The sterilized medium (achieved through autoclaving or irradiation) is inoculated with a spore suspension ($1\times10^2$-$1\times10^7$ cfu/ml) of the appropriate *Penicillium* spp. and the moisture adjusted to 20 to 50%, depending on the substrate. The material is incubated for 2 to 8 weeks at room temperature. The spores may also be produced by liquid fermentation (Cunningham et al., 1990. Can J Bot 68:2270-2274). Liquid production may be achieved by cultivating the fungus in any suitable media, such as potato dextrose broth or sucrose yeast extract media, under appropriate pH and temperature conditions (as could be performed by anyone skilled in the art).

The resulting material may be used directly in a composition, as a seed treatment, or the spores may be harvested, concentrated by centrifugation, formulated, and then dried using air drying, freeze drying, or fluid bed drying techniques (Friesen T., Hill G., Pugsley T., Holloway G., and Zimmerman D. 2005, Experimental determination of viability loss of *Penicillium bilaiae* conidia during convective air-drying Appl Microbiol Biotechnol 68: 397-404) to produce a wettable powder.

Above mentioned deposited strains were deposited on Oct. 1, 2012, as indicated in more detail below, in the "Materials & Methods"-section, under terms of the Budapest Treaty on the International Recognition of the Deposit of Microorganisms for the Purposes of Patent Procedure at the Agricultural Research Service Culture Collection, 1815 North University Street, Peoria, Ill. 61604, U.S.A.

Compositions

In another aspect, the invention relates to a composition comprising a carrier and an inoculum of one or more of the deposited strains (either spore form or strains in a vegetative state) described herein. In certain embodiments, the composition may be in the form of a liquid, a slurry, a solid, or a powder (wettable powder or dry powder). In another embodiment, the composition may be in the form of a seed coating. Compositions in liquid, slurry, or powder (e.g., wettable powder) form may be suitable for coating seeds. When used to coat seeds, the composition may be applied to the seeds and allowed to dry. In embodiments wherein the composition is a powder (e.g., a wettable powder), a liquid, such as water, may need to be added to the powder before application to a seed.

Carriers:

The carriers described herein will allow the deposited fungal strain(s) to remain efficacious (e.g., capable of solubilizing phosphate) and viable once formulated. Non-limiting examples of carriers described herein include liquids, slurries, or solids (including wettable powders or dry powders). In an embodiment, the carrier is a soil compatible carrier as described herein.

In one embodiment, the carrier is a liquid carrier. Non-limiting examples of liquids useful as carriers for the compositions disclosed herein include water, an aqueous solution, or a non-aqueous solution. In one embodiment, the carrier is water. In another embodiment the carrier is an aqueous solution, such as sugar water. In another embodiment, the carrier is a non-aqueous solution. If a liquid carrier is used, the liquid (e.g., water) carrier may further include growth media to culture the deposited fungal strains. Non-limiting examples of suitable growth media for the deposited fungal strains include Czapek-Dox medium or potato dextrose broth, or any media known to those skilled in the art to be compatible with, and/or provide growth nutrients to the deposited fungal strains.

In another embodiment, the carrier is a slurry. In an embodiment, the slurry may comprise a sticking agent, a liquid, or a combination thereof. It is envisioned that the sticking agent can be any agent capable of sticking the inoculum (e.g., one or more of the deposited strains) to a substrate of interest (e.g., a seed). Non-limiting examples of sticking agents include alginate, mineral oil, syrup, gum arabic, honey, methyl cellulose, milk, wallpaper paste, and combinations thereof. Non-limiting examples of liquids appropriate for a slurry include water or sugar water.

In another embodiment, the carrier is a solid. In a particular embodiment the solid is a powder. In one embodiment the powder is a wettable powder. In another embodiment, the powder is a dry powder. In another embodiment, the solid is a granule. Non-limiting examples of solids useful as carriers for the compositions disclosed herein include peat, wheat, wheat chaff, ground wheat straw, bran, vermiculite, cellulose, starch, soil (pasteurized or unpasteurized), gypsum, talc, clays (e.g., kaolin, bentonite, montmorillonite), and silica gels.

Optional Ingredients:

The compositions disclosed herein may comprise one or more optional ingredients. Non-limiting examples of optional ingredients include one or more phosphorus sources, one or more biologically active ingredients, micronutrients, biostimulants, preservatives, polymers, wetting agents, surfactants, or combinations thereof.

Phosphorus Source(s):

The compositions described herein may optionally comprise one or more phosphorus sources. Any source of phosphorus that is capable of being solubilized by the deposited strains may be used.

In one embodiment, the one or more phosphorus sources are rock phosphate.

In another embodiment, the one or more phosphorus sources are fertilizers comprising one or more phosphorus sources. Commercially available manufactured phosphate fertilizers are of many types. Some common ones are those containing rock phosphate, monoammonium phosphate, diammonium phosphate, monocalcium phosphate, super phosphate, triple super phosphate, and/or ammonium polyphosphate. All of these fertilizers are produced by chemical processing of insoluble natural rock phosphates in large scale fertilizer-manufacturing facilities and the product is expensive. By means of the present invention it is possible to reduce the amount of these fertilizers applied to the soil while still maintaining the same amount of phosphorus uptake from the soil.

In still another embodiment, the one or more phosphorus sources are organic phosphorus sources. In a further particular embodiment the source or phosphorus is an organic fertilizer. An organic fertilizer refers to a soil amendment derived from natural sources that guarantees, at least, the minimum percentages of nitrogen, phosphate, and potash. Non-limiting examples of organic fertilizers include plant and animal by-products, rock powders, seaweed, inoculants, and conditioners. These are often available at garden centers and through horticultural supply companies. In particular the organic source of phosphorus is from bone meal, meat meal, animal manure, compost, sewage sludge, or guano, or combinations thereof.

In still another embodiment, the one or more phosphorus sources may be a combination of phosphorus sources including, but not limited to, rock phosphate, monoammonium phosphate, diammonium phosphate, monocalcium phosphate, super phosphate, triple super phosphate, ammonium polyphosphate, fertilizers comprising one or more phosphorus sources, one or more organic phosphorus sources, and combinations thereof.

Biologically Active Ingredient(s):

The fungal compositions described herein may optionally include one or more biologically active ingredients as described herein, other than the fungal pesticides described herein. Non-limiting examples of biologically active ingredients include signal molecules (e.g., lipo-chitooligosaccharides (LCO), chitooligosaccharides (CO), chitinous compounds, flavonoids, jasmonic acid or derivatives thereof, linoleic acid or derivatives thereof, linolenic acid or derivatives thereof, kerrikins, etc.) and beneficial microorganisms (e.g., *Rhizobium* spp., *Bradyrhizobium* spp., *Sinorhizobium* spp., *Azorhizobium* spp., etc.).

Signal Molecule(s):

In an embodiment, the compositions described herein include one or more signal molecules. In one embodiment, the one or more signal molecules are one or more LCOs. In another embodiment, the one or more signal molecules are one or more chitinous compounds. In still another embodiment, the one or more signal molecules are one or more COs. In yet another embodiment, the one or more signal molecules are one or more flavonoids or derivatives thereof. In still yet another embodiment, the one or more signal molecules are one or more non-flavonoid nod gene inducers (e.g., jasmonic acid, linoleic acid, linolenic acid, and derivatives thereof). In still yet another embodiment, the one or more signal molecules are one or more karrikins or derivatives thereof. In still another embodiment, the one or more signal molecules are one or more LCOs, one or more chitinous compounds, one or more COs, one or more flavonoids and derivatives thereof, one or more non-flavonoid nod gene inducers and derivatives thereof, one or more karrikins and derivatives thereof, or any signal molecule combination thereof.

LCOs:

Lipo-chitooligosaccharide compounds (LCOs), also known in the art as symbiotic Nod signals or Nod factors, consist of an oligosaccharide backbone of β-1,4-linked N-acetyl-D-glucosamine ("GlcNAc") residues with an N-linked fatty acyl chain condensed at the non-reducing end. LCO's differ in the number of GlcNAc residues in the backbone, in the length and degree of saturation of the fatty acyl chain, and in the substitutions of reducing and non-reducing sugar residues. An example of an LCO is presented below as formula I:

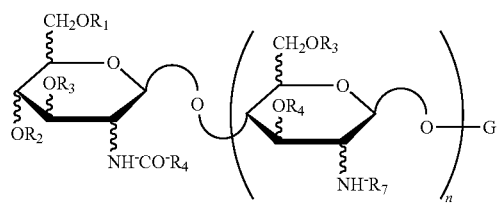

in which:

G is a hexosamine which can be substituted, for example, by an acetyl group on the nitrogen, a sulfate group, an acetyl group and/or an ether group on an oxygen, $R_1$, $R_2$, $R_3$, $R_5$, $R_6$ and $R_7$, which may be identical or different, represent H, $CH_3CO-$, $C_xH_yCO-$ where x is an integer between 0 and 17, and y is an integer between 1 and 35, or any other acyl group such as for example a carbamyl, $R_4$ represents a mono-, di- or triunsaturated aliphatic chain containing at least 12 carbon atoms, and n is an integer between 1 and 4.

LCOs may be obtained (isolated and/or purified) from bacteria such as *Rhizobia*, e.g., *Rhizobium* spp., *Bradyrhizobium* spp., *Sinorhizobium* spp. and *Azorhizobium* spp. LCO structure is characteristic for each such bacterial species, and each strain may produce multiple LCO's with different structures. For example, specific LCOs from *S. meliloti* have also been described in U.S. Pat. No. 5,549,718 as having the formula II:

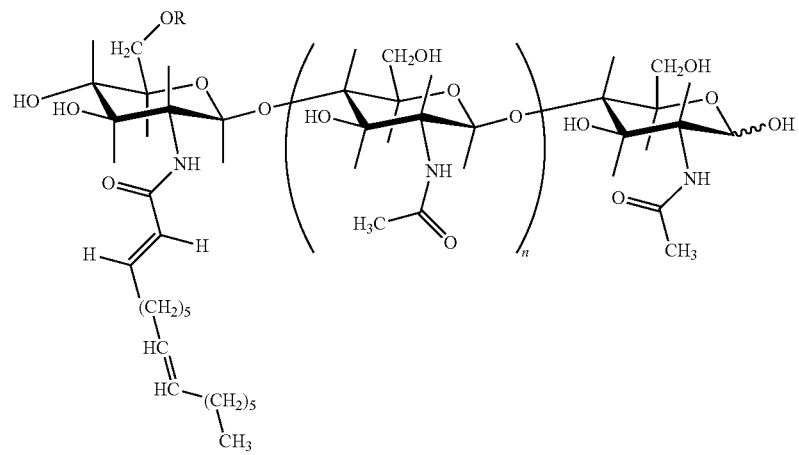

in which R represents H or $CH_3CO-$ and n is equal to 2 or 3.

Even more specific LCOs include NodRM, NodRM-1, NodRM-3. When acetylated (the $R=CH_3CO-$), they become AcNodRM-1, and AcNodRM-3, respectively (U.S. Pat. No. 5,545,718).

LCOs from *Bradyrhizobium japonicum* are described in U.S. Pat. Nos. 5,175,149 and 5,321,011. Broadly, they are pentasaccharide phytohormones comprising methylfucose. A number of these *B. japonicum*-derived LCOs are described: BjNod-V ($C_{18:1}$); BjNod-V (Ac, $C_{18:1}$), BjNod-V ($C_{16:1}$); and BjNod-V (Ac, $C_{16:0}$), with "V" indicating the presence of five N-acetylglucosamines; "Ac" an acetylation; the number following the "C" indicating the number of carbons in the fatty acid side chain; and the number following the ":" the number of double bonds.

LCOs used in compositions of the invention may be obtained (i.e., isolated and/or purified) from bacterial strains that produce LCO's, such as strains of *Azorhizobium, Bradyrhizobium* (including *B. japonicum*), *Mesorhizobium, Rhizobium* (including *R. leguminosarum*), *Sinorhizobium* (including *S. meliloti*), and bacterial strains genetically engineered to produce LCO's.

Also encompassed by the present invention are compositions using LCOs obtained (i.e., isolated and/or purified)

from a mycorrhizal fungus, such as fungi of the group Glomerocycota, e.g., *Glomus intraradicus*. The structures of representative LCOs obtained from these fungi are described in WO 2010/049751 and WO 2010/049751 (the LCOs described therein also referred to as "Myc factors").

Further encompassed by compositions of the present invention is use of synthetic LCO compounds, such as those described in WO 2005/063784, and recombinant LCO's produced through genetic engineering. The basic, naturally occurring LCO structure may contain modifications or substitutions found in naturally occurring LCO's, such as those described in Spaink, Crit. Rev. Plant Sci. 54:257-288 (2000) and D'Haeze, et al., Glycobiology 12:79R-105R (2002). Precursor oligosaccharide molecules (COs, which as described below, are also useful as plant signal molecules in the present invention) for the construction of LCOs may also be synthesized by genetically engineered organisms, e.g., as in Samain, et al., Carb. Res. 302:35-42 (1997); Samain, et al., J. Biotechnol. 72:33-47 (1999).

LCO's may be utilized in various forms of purity and may be used alone or in the form of a culture of LCO-producing bacteria or fungi. Methods to provide substantially pure LCO's include simply removing the microbial cells from a mixture of LCOs and the microbe, or continuing to isolate and purify the LCO molecules through LCO solvent phase separation followed by HPLC chromatography as described, for example, in U.S. Pat. No. 5,549,718. Purification can be enhanced by repeated HPLC, and the purified LCO molecules can be freeze-dried for long-term storage.

COs:

Chitooligosaccharides (COs) are known in the art as β-1-4 linked N acetyl glucosamine structures identified as chitin oligomers, also as N-acetylchitooligosaccharides. CO's have unique and different side chain decorations which make them different from chitin molecules [$(C_8H_{13}NO_5)n$, CAS No. 1398-61-4], and chitosan molecules [$(C_5H_{11}NO_4)n$, CAS No. 9012-76-4]. Representative literature describing the structure and production of COs is as follows: Van der Hoist, et al., Current Opinion in Structural Biology, 11:608-616 (2001); Robina, et al., Tetrahedron 58:521-530 (2002); Hanel, et al., Planta 232:787-806 (2010); Rouge, et al. Chapter 27, "The Molecular Immunology of Complex Carbohydrates" in Advances in Experimental Medicine and Biology, Springer Science; Wan, et al., Plant Cell 21:1053-69 (2009); PCT/F100/00803 (Sep. 21, 2000); and Demont-Caulet, et al., Plant Physiol. 120(1):83-92 (1999). The COs may be synthetic or recombinant. Methods for preparation of recombinant COs are known in the art. See, e.g., Samain, et al. (supra.); Cottaz, et al., Meth. Eng. 7(4):311-7 (2005) and Samain, et al., J. Biotechnol. 72:33-47 (1999).

Chitinous Compounds:

Chitins and chitosans, which are major components of the cell walls of fungi and the exoskeletons of insects and crustaceans, are also composed of GlcNAc residues. Chitinous compounds include chitin, (IUPAC: N-[5-[[3-acetylamino-4,5-dihydroxy-6-(hydroxymethyl)oxan-2yl]methoxymethyl]-2-[[5-acetylamino-4,6-dihydroxy-2-(hydroxymethyl)oxan-3-yl]methoxymethyl]-4-hydroxy-6-(hydroxymethyl)oxan-3-ys]ethanamide), and chitosan, (IUPAC: 5-amino-6-[5-amino-6-[5-amino-4,6-dihydroxy-2-(hydroxymethyl)oxan-3-yl]oxy-4-hydroxy-2-(hydroxymethyl)oxan-3-yl]oxy-2(hydroxymethyl)oxane-3,4-diol).

These compounds may be obtained commercially, e.g., from Sigma-Aldrich, or prepared from insects, crustacean shells, or fungal cell walls. Methods for the preparation of chitin and chitosan are known in the art, and have been described, for example, in U.S. Pat. No. 4,536,207 (preparation from crustacean shells), Pochanavanich, et al., Lett. Appl. Microbiol. 35:17-21 (2002) (preparation from fungal cell walls), and U.S. Pat. No. 5,965,545 (preparation from crab shells and hydrolysis of commercial chitosan). Deacetylated chitins and chitosans may be obtained that range from less than 35% to greater than 90% deacetylation, and cover a broad spectrum of molecular weights, e.g., low molecular weight chitosan oligomers of less than 15 kD and chitin oligomers of 0.5 to 2 kD; "practical grade" chitosan with a molecular weight of about 15 kD; and high molecular weight chitosan of up to 70 kD. Chitin and chitosan compositions formulated for seed treatment are also commercially available. Commercial products include, for example, ELEXA® (Plant Defense Boosters, Inc.) and BEYOND™ (Agrihouse, Inc.).

Flavonoids:

Flavonoids are phenolic compounds having the general structure of two aromatic rings connected by a three-carbon bridge. Flavonoids are produced by plants and have many functions, e.g., as beneficial signaling molecules, and as protection against insects, animals, fungi and bacteria. Classes of flavonoids include chalcones, anthocyanidins, coumarins, flavones, flavanols, flavonols, flavanones, and isoflavones. See, Jain, et al., J. Plant Biochem. & Biotechnol. 11:1-10 (2002); Shaw, et al., Environmental Microbiol. 11:1867-80 (2006).

Representative flavonoids that may be useful in compositions of the present invention include luteolin, apigenin, tangeritin, quercetin, kaempferol, myricetin, fisetin, isorhamnetin, pachypodol, rhamnazin, hesperetin, naringenin, formononetin, eriodictyol, homoeriodictyol, taxifolin, dihydroquercetin, dihydrokaempferol, genistein, daidzein, glycitein, catechin, gallocatechin, catechin 3-gallate, gallocatechin 3-gallate, epicatechin, epigallocatechin, epicatechin 3-gallate, epigallocatechin 3-gallate, cyaniding, delphinidin, malvidin, pelargonidin, peonidin, petunidin, or derivatives thereof. Flavonoid compounds are commercially available, e.g., from Natland International Corp., Research Triangle Park, N.C.; MP Biomedicals, Irvine, Calif.; LC Laboratories, Woburn Mass. Flavonoid compounds may be isolated from plants or seeds, e.g., as described in U.S. Pat. Nos. 5,702,752; 5,990,291; and 6,146,668. Flavonoid compounds may also be produced by genetically engineered organisms, such as yeast, as described in Ralston, et al., Plant Physiology 137:1375-88 (2005).

Non-Flavonoid Nod-Gene Inducer(s):

Jasmonic acid (JA, [1R-[1α,2β(Z)]]-3-oxo-2-(pentenyl) cyclopentaneacetic acid) and its derivatives, linoleic acid ((Z,Z)-9,12-Octadecadienoic acid) and its derivatives, and linolenic acid ((Z,Z,Z)-9,12,15-octadecatrienoic acid) and its derivatives, may also be used in compositions of the present invention. Jasmonic acid and its methyl ester, methyl jasmonate (MeJA), collectively known as jasmonates, are octadecanoid-based compounds that occur naturally in plants. Jasmonic acid is produced by the roots of wheat seedlings, and by fungal microorganisms such as *Botryodiplodia theobromae* and *Gibberella fujikuroi*, yeast (*Saccharomyces cerevisiae*), and pathogenic and non-pathogenic strains of *Escherichia coli*. Linoleic acid and linolenic acid are produced in the course of the biosynthesis of jasmonic acid. Jasmonates, linoleic acid and linoleic acid (and their derivatives) are reported to be inducers of nod gene expression or LCO production by rhizobacteria. See, e.g., Mabood, Fazli, Jasmonates induce the expression of nod genes in *Bradyrhizobium japonicum*, May 17, 2001; and Mabood, Fazli, "Linoleic and linolenic acid induce the expression of nod genes in *Bradyrhizobium japonicum*," USDA 3, May 17, 2001.

Useful derivatives of linoleic acid, linolenic acid, and jasmonic acid that may be useful in compositions of the present invention include esters, amides, glycosides and salts. Representative esters are compounds in which the carboxyl group of linoleic acid, linolenic acid, or jasmonic acid has been replaced with a —COR group, where R is an —OR$^1$ group, in which R$^1$ is: an alkyl group, such as a $C_1$-$C_8$ unbranched or branched alkyl group, e.g., a methyl, ethyl or propyl group; an alkenyl group, such as a $C_2$-$C_8$ unbranched or branched alkenyl group; an alkynyl group, such as a $C_2$-$C_8$ unbranched or branched alkynyl group; an aryl group having, for example, 6 to 10 carbon atoms; or a heteroaryl group having, for example, 4 to 9 carbon atoms, wherein the heteroatoms in the heteroaryl group can be, for example, N, O, P, or S. Representative amides are compounds in which the carboxyl group of linoleic acid, linolenic acid, or jasmonic acid has been replaced with a —COR group, where R is an NR$^2$R$^3$ group, in which R$^2$ and R$^3$ are independently: hydrogen; an alkyl group, such as a $C_1$-$C_8$ unbranched or branched alkyl group, e.g., a methyl, ethyl or propyl group; an alkenyl group, such as a $C_2$-$C_8$ unbranched or branched alkenyl group; an alkynyl group, such as a $C_2$-$C_8$ unbranched or branched alkynyl group; an aryl group having, for example, 6 to 10 carbon atoms; or a heteroaryl group having, for example, 4 to 9 carbon atoms, wherein the heteroatoms in the heteroaryl group can be, for example, N, O, P, or S. Esters may be prepared by known methods, such as acid-catalyzed nucleophilic addition, wherein the carboxylic acid is reacted with an alcohol in the presence of a catalytic amount of a mineral acid. Amides may also be prepared by known methods, such as by reacting the carboxylic acid with the appropriate amine in the presence of a coupling agent such as dicyclohexyl carbodiimide (DCC), under neutral conditions. Suitable salts of linoleic acid, linolenic acid, and jasmonic acid include e.g., base addition salts. The bases that may be used as reagents to prepare metabolically acceptable base salts of these compounds include those derived from cations such as alkali metal cations (e.g., potassium and sodium) and alkaline earth metal cations (e.g., calcium and magnesium). These salts may be readily prepared by mixing together a solution of linoleic acid, linolenic acid, or jasmonic acid with a solution of the base. The salt may be precipitated from solution and be collected by filtration or may be recovered by other means such as by evaporation of the solvent.

Karrikin(s):

Karrikins are vinylogous 4H-pyrones e.g., 2H-furo[2,3-c]pyran-2-ones including derivatives and analogues thereof. Examples of these compounds are represented by the following structure:

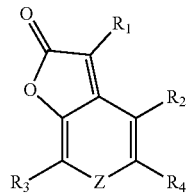

wherein; Z is O, S or NR$_5$; R$_1$, R$_2$, R$_3$, and R$_4$ are each independently H, alkyl, alkenyl, alkynyl, phenyl, benzyl, hydroxy, hydroxyalkyl, alkoxy, phenyloxy, benzyloxy, CN, COR$_6$, COOR—, halogen, NR$_6$R$_7$, or NO$_2$; and R$_5$, R$_6$, and R$_7$ are each independently H, alkyl or alkenyl, or a biologically acceptable salt thereof. Examples of biologically acceptable salts of these compounds may include acid addition salts formed with biologically acceptable acids, examples of which include hydrochloride, hydrobromide, sulphate or bisulphate, phosphate or hydrogen phosphate, acetate, benzoate, succinate, fumarate, maleate, lactate, citrate, tartrate, gluconate; methanesulphonate, benzenesulphonate and p-toluenesulphonic acid. Additional biologically acceptable metal salts may include alkali metal salts, with bases, examples of which include the sodium and potassium salts. Examples of compounds embraced by the structure and which may be suitable for use in the present invention include the following: 3-methyl-2H-furo[2,3-c]pyran-2-one (where R$_1$=CH$_3$, R$_2$, R$_3$, R$_4$=H), 2H-furo[2,3-c]pyran-2-one (where R$_1$, R$_2$, R$_3$, R4=H), 7-methyl-2H-furo[2,3-c]pyran-2-one (where R$_1$, R$_2$, R$_4$=H, R$_3$=CH$_3$), 5-methyl-2H-furo[2,3-c]pyran-2-one (where R$_1$, R$_2$, R$_3$=H, R$_4$=CH$_3$), 3,7-dimethyl-2H-furo[2,3-c]pyran-2-one (where R$_1$, R$_3$=CH$_3$, R$_2$, R$_4$=H), 3,5-dimethyl-2H-furo[2,3-c]pyran-2-one (where R$_1$, R$_4$=CH$_3$, R$_2$, R$_3$=H), 3,5,7-trimethyl-2H-furo[2,3-c]pyran-2-one (where R$_1$, R$_3$, R$_4$=CH$_3$, R$_2$=H), 5-methoxymethyl-3-methyl-2H-furo[2,3-c]pyran-2-one (where R$_1$=CH$_3$, R$_2$, R$_3$=H, R$_4$=CH$_2$OCH$_3$), 4-bromo-3,7-dimethyl-2H-furo[2,3-c]pyran-2-one (where R$_1$, R$_3$=CH$_3$, R$_2$=Br, R$_4$=H), 3-methylfuro[2,3-c]pyridin-2(3H)-one (where Z=NH, R$_1$=CH$_3$, R$_2$, R$_3$, R$_4$=H), 3,6-dimethylfuro[2,3-c]pyridin-2(6H)-one (where Z=N—CH$_3$, R$_1$=CH$_3$, R$_2$, R$_3$, R$_4$=H). See, U.S. Pat. No. 7,576,213. These molecules are also known as karrikins. See, Halford, "Smoke Signals," in Chem. Eng. News (Apr. 12, 2010), at pages 37-38 (reporting that karrikins or butenolides which are contained in smoke act as growth stimulants and spur seed germination after a forest fire, and can invigorate seeds such as corn, tomatoes, lettuce and onions that had been stored). These molecules are the subject of U.S. Pat. No. 7,576,213.

Beneficial Microorganism(s):

In an embodiment, the compositions described herein may comprise one or more beneficial microorganisms. The one or more beneficial microorganisms may have one or more beneficial properties (e.g., produce one or more of the signal molecules described herein, enhance nutrient and water uptake, promote and/or enhance nitrogen fixation, enhance growth, enhance seed germination, enhance seedling emergence, break the dormancy or quiescence of a plant, etc.).

In one embodiment, the beneficial microorganism(s) is one or more bacteria. In another embodiment the bacteria are diazotrophs (i.e., bacteria which are symbiotic nitrogen-fixing bacteria). In still another embodiment, the bacteria are bacteria from the genera *Rhizobium* spp. (e.g., *R. cellulosilyticum*, *R. daejeonense*, *R. etli*, *R. galegae*, *R. gallicum*, *R. giardinii*, *R. hainanense*, *R. huautlense*, *R. indigoferae*, *R. leguminosarum*, *R. loessense*, *R. lupini*, *R. lusitanum*, *R. meliloti*, *R. mongolense*, *R. miluonense*, *R. sullae*, *R. tropici*, *R. undicola*, and/or *R. yanglingense*), *Bradyrhizobium* spp. (e.g., *B. bete*, *B. canariense*, *B. elkanii*, *B. iriomotense*, *B. japonicum*, *B. jicamae*, *B. liaoningense*, *B. pachyrhizi*, and/or *B. yuanmingense*), *Azorhizobium* spp. (e.g., *A. caulinodans* and/or *A. doebereinerae*), *Sinorhizobium* spp. (e.g., *S. abri*, *S. adhaerens*, *S. americanum*, *S. aboris*, *S. fredii*, *S. indiaense*, *S. kostiense*, *S. kummerowiae*, *S. medicae*, *S. meliloti*, *S. mexicanus*, *S. morelense*, *S. saheli*, *S. terangae*, and/or *S. xinjiangense*), *Mesorhizobium* spp (*M. albiziae*, *M. amorphae*, *M. chacoense*, *M. ciceri*, *M. huakuii*, *M. loti*, *M.*

*mediterraneum, M. pluifarium, M. septentrionale, M. temperatum*, and/or *M. tianshanense*), and combinations thereof. In a particular embodiment, the beneficial microorganism is selected from the group consisting of *B. japonicum, R leguminosarum, R meliloti, S. meliloti*, and combinations thereof. In another embodiment, the beneficial microorganism is *B. japonicum*. In another embodiment, the beneficial microorganism is *R leguminosarum*. In another embodiment, the beneficial microorganism is *R meliloti*. In another embodiment, the beneficial microorganism is *S. meliloti*.

In another embodiment the beneficial microorganism is one or more mycorrhiza. In particular, the one or more mycorrhiza is an endomycorrhiza (also called vesicular arbuscular mycorrhizas, VAMs, arbuscular mycorrhizas, or AMs), an ectomycorrhiza, or a combination thereof.

In one embodiment, the one or more mycorrhiza is an endomycorrhiza of the phylum Glomeromycota and genera *Glomus* and *Gigaspora*. In still a further embodiment, the endomycorrhiza is a strain of *Glomus aggregatum, Glomus brasilianum, Glomus clarum, Glomus deserticola, Glomus etunicatum, Glomus fasciculatum, Glomus intraradices, Glomus monosporum*, or *Glomus mosseae, Gigaspora margarita*, or a combination thereof.

In another embodiment, the one or more mycorrhiza is an ectomycorrhiza of the phylum Basidiomycota, Ascomycota, and Zygomycota. In still yet another embodiment, the ectomycorrhiza is a strain of *Laccaria bicolor, Laccaria laccata, Pisolithus tinctorius, Rhizopogon amylopogon, Rhizopogon fulvigleba, Rhizopogon luteolus, Rhizopogon villosuli, Scleroderma cepa, Scleroderma citrinum*, or a combination thereof.

In still another embodiment, the one or more mycorrhiza is an ericoid mycorrhiza, an arbutoid mycorrhiza, or a monotropoid mycorrhiza. Arbuscular and ectomycorrhizas form ericoid mycorrhiza with many plants belonging to the order Ericales, while some Ericales form arbutoid and monotropoid mycorrhizas. All orchids are mycoheterotrophic at some stage during their lifecycle and form orchid mycorrhizas with a range of basidiomycete fungi. In one embodiment, the mycorrhiza may be an ericoid mycorrhiza, preferably of the phylum Ascomycota, such as *Hymenoscyphous ericae* or *Oidiodendron* sp. In another embodiment, the mycorrhiza also may be an arbutoid mycorrhiza, preferably of the phylum Basidiomycota. In yet another embodiment, the mycorrhiza may be a monotripoid mycorrhiza, preferably of the phylum Basidiomycota. In still yet another embodiment, the mycorrhiza may be an orchid mycorrhiza, preferably of the genus *Rhizoctonia*.

Micronutrient(s):

In still another embodiment, the compositions described herein may comprise one or more beneficial micronutrients. Non-limiting examples of micronutrients for use in the compositions described herein include vitamins, (e.g., vitamin A, vitamin B complex (i.e., vitamin $B_1$, vitamin $B_2$, vitamin $B_3$, vitamin Bs, vitamin $B_6$, vitamin $B_7$, vitamin $B_8$, vitamin $B_9$, vitamin $B_{12}$, choline) vitamin C, vitamin D, vitamin E, vitamin K, carotenoids (α-carotene, β-carotene, cryptoxanthin, lutein, lycopene, zeaxanthin, etc.), macrominerals (e.g., calcium, magnesium, potassium, sodium, iron, etc.), trace minerals (e.g., boron, cobalt, chloride, chromium, copper, fluoride, iodine, iron, manganese, molybdenum, selenium, zinc, etc.) organic acids (e.g., acetic acid, citric acid, lactic acid, malic acid, taurine, etc.) and combinations thereof.

In a particular embodiment, the compositions comprise boron, chlorine, copper, iron, manganese, molybdenum, zinc or combinations thereof.

Biostimulant(s):

In one embodiment, the compositions described herein may comprise one or more beneficial biostimulants. Biostimulants may enhance metabolic or physiological processes such as respiration, photosynthesis, nucleic acid uptake, ion uptake, nutrient delivery, or a combination thereof. Non-limiting examples of biostimulants include seaweed extracts (e.g., *ascophyllum nodosum*), humic acids (e.g., potassium humate), fulvic acids, myo-inositol, glycine, and combinations thereof. In another embodiment, the compositions comprise seaweed extracts, humic acids, fulvic acids, myo-inositol, glycine, and combinations thereof.

Polymer(s):

In one embodiment, the compositions described herein may further comprise one or more polymers. Non-limiting uses of polymers in the agricultural industry include agrochemical delivery, heavy metal removal, water retention and/or water delivery, and combinations thereof. Pouci, et al., Am. J. Agri. & Biol. Sci., 3(1):299-314 (2008). In one embodiment, the one or more polymers is a natural polymer (e.g., agar, starch, alginate, pectin, cellulose, etc.), a synthetic polymer, a biodegradable polymer (e.g., polycaprolactone, polylactide, poly (vinyl alcohol), etc.), or a combination thereof.

For a non-limiting list of polymers useful for the compositions described herein, see Pouci, et al., Am. J. Agri. & Biol. Sci., 3(1):299-314 (2008). In one embodiment, the compositions described herein comprise cellulose, cellulose derivatives, methylcellulose, methylcellulose derivatives, starch, agar, alginate, pectin, polyvinylpyrrolidone, and combinations thereof.

Wetting Agent(s):

In one embodiment, the compositions described herein may further comprise one or more wetting agents. Wetting agents are commonly used on soils, particularly hydrophobic soils, to improve the infiltration and/or penetration of water into a soil. The wetting agent may be an adjuvant, oil, surfactant, buffer, acidifier, or combination thereof. In an embodiment, the wetting agent is a surfactant. In an embodiment, the wetting agent is one or more nonionic surfactants, one or more anionic surfactants, or a combination thereof. In yet another embodiment, the wetting agent is one or more nonionic surfactants.

Surfactants suitable for the compositions described herein are provided in the "Surfactants" section.

Surfactant(s):

Surfactants suitable for the compositions described herein may be non-ionic surfactants (e.g., semi-polar and/or anionic and/or cationic and/or zwitterionic). It is envisioned that the surfactant(s) will cause as little harm to the activity of the one or more deposited strains and/or the one or more beneficial microorganisms as possible. The surfactants can wet and emulsify soil(s) and/or dirt(s). It is envisioned that the surfactants used in described composition have low toxicity for the microorganisms contained within the formulation. It is further envisioned that the surfactants used in the described composition have a low phytotoxicity (i.e., the degree of toxicity a substance or combination of substances has on a plant). A single surfactant or a blend of several surfactants can be used.

Anionic Surfactants

Anionic surfactants or mixtures of anionic and nonionic surfactants may also be used in the compositions. Anionic surfactants are surfactants having a hydrophilic moiety in an anionic or negatively charged state in aqueous solution. The compositions described herein may comprise one or more anionic surfactants. The anionic surfactant(s) may be either water soluble anionic surfactants, water insoluble anionic surfactants, or a combination of water soluble anionic surfactants and water insoluble anionic surfactants. Non-limiting examples of anionic surfactants include sulfonic acids, sulfuric acid esters, carboxylic acids, and salts thereof. Non-limiting examples of water soluble anionic surfactants include alkyl sulfates, alkyl ether sulfates, alkyl amido ether sulfates, alkyl aryl polyether sulfates, alkyl aryl sulfates, alkyl aryl sulfonates, monoglyceride sulfates, alkyl sulfonates, alkyl amide sulfonates, alkyl aryl sulfonates, benzene sulfonates, toluene sulfonates, xylene sulfonates, cumene sulfonates, alkyl benzene sulfonates, alkyl diphenyloxide sulfonate, alpha-olefin sulfonates, alkyl naphthalene sulfonates, paraffin sulfonates, lignin sulfonates, alkyl sulfosuccinates, ethoxylated sulfosuccinates, alkyl ether sulfosuccinates, alkylamide sulfosuccinates, alkyl sulfosuccinamate, alkyl sulfoacetates, alkyl phosphates, phosphate ester, alkyl ether phosphates, acyl sarconsinates, acyl isethionates, N-acyl taurates, N-acyl-N-alkyltaurates, alkyl carboxylates, or a combination thereof.

Nonionic Surfactants

Nonionic surfactants are surfactants having no electrical charge when dissolved or dispersed in an aqueous medium. In at least one embodiment of the composition described herein, one or more nonionic surfactants are used as they provide the desired wetting and emulsification actions and do not significantly inhibit spore stability and activity. The nonionic surfactant(s) may be either water soluble nonionic surfactants, water insoluble nonionic surfactants, or a combination of water soluble nonionic surfactants and water insoluble nonionic surfactants.

Water Insoluble Nonionic Surfactants

Non-limiting examples of water insoluble nonionic surfactants include alkyl and aryl: glycerol ethers, glycol ethers, ethanolamides, sulfoanylamides, alcohols, amides, alcohol ethoxylates, glycerol esters, glycol esters, ethoxylates of glycerol ester and glycol esters, sugar-based alkyl polyglycosides, polyoxyethylenated fatty acids, alkanolamine condensates, alkanolamides, tertiary acetylenic glycols, polyoxyethylenated mercaptans, carboxylic acid esters, polyoxyethylenated polyoxyproylene glycols, sorbitan fatty esters, or combinations thereof. Also included are EO/PO block copolymers (EO is ethylene oxide, PO is propylene oxide), EO polymers and copolymers, polyamines, and polyvinylpynolidones.

Water Soluble Nonionic Surfactants

Non-limiting examples of water soluble nonionic surfactants include sorbitan fatty acid alcohol ethoxylates and sorbitan fatty acid ester ethoxylates.

Combination of Nonionic Surfactants

In one embodiment, the compositions described herein comprise at least one or more nonionic surfactants. In one embodiment, the compositions comprise at least one water insoluble nonionic surfactant and at least one water soluble nonionic surfactant. In still another embodiment, the compositions comprise a combination of nonionic surfactants having hydrocarbon chains of substantially the same length.

Other Surfactants

In another embodiment, the compositions described herein may also comprise organosilicone surfactants, silicone-based antifoams used as surfactants in silicone-based and mineral-oil based antifoams. In yet another embodiment, the compositions described herein may also comprise alkali metal salts of fatty acids (e.g., water soluble alkali metal salts of fatty acids and/or water insoluble alkali metal salts of fatty acids).

Herbicide(s):

In one embodiment, the compositions described herein may further comprise one or more herbicides. In a particular embodiment, the herbicide may be a pre-emergent herbicide, a post-emergent herbicide, or a combination thereof.

Suitable herbicides include chemical herbicides, natural herbicides (e.g., bioherbicides, organic herbicides, etc.), or combinations thereof. Non-limiting examples of suitable herbicides include bentazon, acifluorfen, chlorimuron, lactofen, clomazone, fluazifop, glufosinate, glyphosate, sethoxydim, imazethapyr, imazamox, fomesafe, flumiclorac, imazaquin, clethodim, pendimethalin; 3,4-Dimethyl-2,6-dinitro-N-pentan-3-yl-aniline; N-(1-ethylpropyl)-2,6-dinitro-3,4-xylidine; pronamide; propyzamide; 3,5-Dichloro-N-(1,1-dimethylpropynyl)benzamide; 3,5-Dichloro-N-(1,1-dimethyl-2-propynyl)benzamide; N-(1,1-Dimethylpropynyl)-3,5-dichlorobenzamide; S-ethyl N-ethylthiocyclohexanecarbamate; trifluralin; 2,6-Dinitro-N,N-dipropyl-4-(trifluoromethyl)aniline; glyphosate; N-(phosphonomethyl)glycine; and derivatives thereof. In one embodiment, the one or more herbicides for use in accordance with this disclosure include pronamide (commercially referred to as Kerb®); propyzamide; 3,5-Dichloro-N-(1,1-dimethylpropynyl)benzamide; 3,5-Dichloro-N-(1,1-dimethyl-2-propynyl)benzamide; N-(1,1-Dimethylpropynyl)-3,5-dichlorobenzamide; cycloate, S-ethyl N-ethylthiocyclohexanecarbamate (commercially referred to as Ro-Neet®); trifluralin; 2,6-Dinitro-N,N-dipropyl-4-(trifluoromethyl)aniline; glyphosate; N-(phosphonomethyl)glycine; and derivatives thereof. Commercial products containing each of these compounds are readily available. Herbicide concentration in the composition will generally correspond to the labeled use rate for a particular herbicide.

Fungicide(s):

In one embodiment, the compositions described herein may further comprise one or more fungicides. Fungicides useful to the compositions described herein will suitably exhibit activity against a broad range of pathogens, including but not limited to *Phytophthora, Rhizoctonia, Fusarium, Pythium, Phomopsis* or *Selerotinia* and *Phakopsora* and combinations thereof.

Non-limiting examples of commercial fungicides which may be suitable for the compositions disclosed herein include PROTÉGÉ, RIVAL or ALLEGIANCE FL or LS (Gustafson, Plano, Tex.), WARDEN RTA (Agrilance, St. Paul, Minn.), APRON XL, APRON MAXX RTA or RFC, MAXIM 4FS or XL (Syngenta, Wilmington, Del.), CAPTAN (Arvesta, Guelph, Ontario) and PROTREAT (Nitragin Argentina, Buenos Ares, Argentina). Active ingredients in these and other commercial fungicides include, but are not limited to, fludioxonil, mefenoxam, azoxystrobin and metalaxyl. Commercial fungicides are most suitably used in accordance with the manufacturer's instructions at the recommended concentrations.

Insecticide(s):

In one embodiment, the compositions described herein may further comprise one or more insecticides. Insecticides useful to the compositions described herein will suitably exhibit activity against a broad range of insects including, but not limited to, wireworms, cutworms, grubs, corn rootworm, seed corn maggots, flea beetles, chinch bugs, aphids, leaf beetles, stink bugs, and combinations thereof.

Non-limiting examples of commercial insecticides which may be suitable for the compositions disclosed herein include CRUISER (Syngenta, Wilmington, Del.), GAUCHO and PONCHO (Gustafson, Plano, Tex.). Active ingredients in these and other commercial insecticides include thiamethoxam, clothianidin, and imidacloprid. Commercial insecticides are most suitably used in accordance with the manufacturer's instructions at the recommended concentrations.

Methods

In another aspect, methods of using the deposited strains and compositions described herein are disclosed.

In one embodiment a method for increasing the availability of phosphorus for plant uptake from soil is described. The method comprises introducing into the soil one or more fungal strains selected from the group consisting of:
the strain having the deposit accession number NRRL B-50776,
the strain having the deposit accession number NRRL B-50777,
the strain having the deposit accession number NRRL B-50778,
the strain having the deposit accession number NRRL B-50779,
the strain having the deposit accession number NRRL B-50780,
the strain having the deposit accession number NRRL B-50781,
the strain having the deposit accession number NRRL B-50782,
the strain having the deposit accession number NRRL B-50783,
the strain having the deposit accession number NRRL B-50784,
the strain having the deposit accession number NRRL B-50785,
the strain having the deposit accession number NRRL B-50786,
the strain having the deposit accession number NRRL B-50787,
the strain having the deposit accession number NRRL B-50788, and
a mixture of two or more of the strains thereof.

In a particular embodiment, the method comprises introducing an inoculum of one or more of the above mentioned deposited strains (e.g., including at least two of the above strains, at least three of the above strains, at least four of the above strains, at least five of the above strains, at least six of the above strains, at least seven of the above strains, at least eight of the above strains, at least nine of the above strains, at least ten of the above strains, at least eleven of the above strains, at least twelve of the above strains, up to and including all of the above strains).

In an embodiment, the inoculum comprises the strain having the deposit accession number NRRL B-50776. In an embodiment, the inoculum comprises the strain having the deposit accession number NRRL B-50777. In an embodiment, the inoculum comprises the strain having the deposit accession number NRRL B-50778. In an embodiment, the inoculum comprises the strain having the deposit accession number NRRL B-50779. In an embodiment, the inoculum comprises the strain having the deposit accession number NRRL B-50780. In an embodiment, the inoculum comprises the strain having the deposit accession number NRRL B-50781. In an embodiment, the inoculum comprises the strain having the deposit accession number NRRL B-50782. In an embodiment, the inoculum comprises the strain having the deposit accession number NRRL B-50783. In an embodiment, the inoculum comprises the strain having the deposit accession number NRRL B-50784. In an embodiment, the inoculum comprises the strain having the deposit accession number NRRL B-50785. In an embodiment, the inoculum comprises the strain having the deposit accession number NRRL B-50786. In an embodiment, the inoculum comprises the strain having the deposit accession number NRRL B-50787. In an embodiment, the inoculum comprises the strain having the deposit accession number NRRL B-50788.

In still another embodiment, the step of introducing into the soil an inoculum of one or more of the deposited fungal strains comprises introducing into the soil one or more of the compositions described herein. The inoculum(s) or compositions may be introduced into the soil according to methods known to those skilled in the art. Non-limiting examples include in-furrow introduction, spraying, coating seeds, foliar introduction, etc. In a particular embodiment, the introducing step comprises in-furrow introduction of the inoculum or compositions described herein.

In some embodiments, the step of introducing into the soil one or more of the deposited fungal strains comprises introducing an effective amount of the one or more of the deposited fungal strains. In certain embodiments, the step of introducing into the soil an inoculum of one or more of the deposited fungal strains comprises introducing the inoculum into the soil in an amount of $1\times10^1$-$1\times10^8$, more preferably $1\times10^6$-$1\times10^{12}$ colony forming units per hectare. In other certain embodiments, the step of introducing into the soil an inoculum of one or more of the deposited fungal strains comprises introducing the deposited fungal strains as a seed coated with $1\times10^1$-$1\times10^8$, more preferably $1\times10^2$-$1\times10^6$ colony forming units per seed.

Further still, the method may comprise contacting the fungal strain with one or more phosphorus sources, e.g., by adding one or more phosphorus sources to the soil. The step of adding a phosphorus source may occur before, after, or during the step of introducing an inoculum into the soil. In still another embodiment, the one or more phosphorus sources may be an ingredient in a composition described herein. According to the method described herein, any source of phosphorus that is capable of being solubilized by the deposited strains may be used.

In one embodiment, the one or more phosphorus sources are rock phosphate.

In another embodiment, the one or more phosphorus sources are fertilizers comprising one or more phosphorus sources. Commercially available manufactured phosphate fertilizers are of many types. Some common ones are those containing rock phosphate, monoammonium phosphate, diammonium phosphate, monocalcium phosphate, super phosphate, triple super phosphate, and/or ammonium polyphosphate. All of these fertilizers are produced by chemical processing of insoluble natural rock phosphates in large scale fertilizer-manufacturing facilities and the product is expensive. By means of the present invention it is possible to reduce the amount of these fertilizers applied to the soil while still maintaining the same amount of phosphorus uptake from the soil.

In still another embodiment, the one or more phosphorus sources are organic phosphorus sources. In a further particular embodiment the source or phosphorus is an organic fertilizer. An organic fertilizer refers to a soil amendment derived from natural sources that guarantees, at least, the minimum percentages of nitrogen, phosphate, and potash. Non-limiting examples of organic fertilizers include plant and animal by-products, rock powders, seaweed, inoculants, and conditioners. These are often available at garden centers and through horticultural supply companies. In particular the organic source of phosphorus is from bone meal, meat meal, animal manure, compost, sewage sludge, or guano, or combinations thereof.

In still yet another embodiment, the one or more phosphorus sources may be a combination of phosphorus sources including, but not limited to, rock phosphate, monoammonium phosphate, diammonium phosphate, monocalcium phosphate, super phosphate, triple super phosphate, ammonium polyphosphate, fertilizers comprising one or more phosphorus sources, one or more organic phosphorus sources, and combinations thereof.

In another aspect, the method comprises growing plants in a soil comprising one or more phosphorus sources and one or more fungal strains selected from the group consisting of:
the strain having the deposit accession number NRRL B-50776,
the strain having the deposit accession number NRRL B-50777,
the strain having the deposit accession number NRRL B-50778,
the strain having the deposit accession number NRRL B-50779,
the strain having the deposit accession number NRRL B-50780,
the strain having the deposit accession number NRRL B-50781,
the strain having the deposit accession number NRRL B-50782,
the strain having the deposit accession number NRRL B-50783,
the strain having the deposit accession number NRRL B-50784,
the strain having the deposit accession number NRRL B-50785,
the strain having the deposit accession number NRRL B-50786,
the strain having the deposit accession number NRRL B-50787,
the strain having the deposit accession number NRRL B-50788, and
a mixture of two or more of the strains thereof.

In a particular embodiment, the method comprises an inoculum of one or more of the above mentioned deposited strains (e.g., including at least two of the above strains, at least three of the above strains, at least four of the above strains, at least five of the above strains, at least six of the above strains, at least seven of the above strains, at least eight of the above strains, at least nine of the above strains, at least ten of the above strains, at least eleven of the above strains, at least twelve of the above strains, up to and including all of the above strains).

In an embodiment, the inoculum comprises the strain having the deposit accession number NRRL B-50776. In an embodiment, the inoculum comprises the strain having the deposit accession number NRRL B-50777. In an embodiment, the inoculum comprises the strain having the deposit accession number NRRL B-50778. In an embodiment, the inoculum comprises the strain having the deposit accession number NRRL B-50779. In an embodiment, the inoculum comprises the strain having the deposit accession number NRRL B-50780. In an embodiment, the inoculum comprises the strain having the deposit accession number NRRL B-50781. In an embodiment, the inoculum comprises the strain having the deposit accession number NRRL B-50782. In an embodiment, the inoculum comprises the strain having the deposit accession number NRRL B-50783. In an embodiment, the inoculum comprises the strain having the deposit accession number NRRL B-50784. In an embodiment, the inoculum comprises the strain having the deposit accession number NRRL B-50785. In an embodiment, the inoculum comprises the strain having the deposit accession number NRRL B-50786. In an embodiment, the inoculum comprises the strain having the deposit accession number NRRL B-50787. In an embodiment, the inoculum comprises the strain having the deposit accession number NRRL B-50788.

In a particular embodiment, the step of introducing into the soil one or more of the deposited fungal strains comprises introducing into the soil one or more of the compositions described herein. In some embodiments, the composition comprises an effective amount of the one or more of the deposited fungal strains. In certain embodiments, the step of introducing into the soil an inoculum of one or more of the deposited fungal strains comprises introducing the inoculum into the soil in an amount of $1\times10^1$-$1\times10^8$, more preferably $1\times10^6$-$1\times10^{12}$ colony forming units per hectare. In other certain embodiments, the step of introducing into the soil an inoculum of one or more of the deposited fungal strains comprises introducing the deposited fungal strains as a seed coated with $1\times10^1$-$1\times10^8$, more preferably $1\times10^2$-$1\times10^6$ colony forming units per seed.

In an embodiment, the method further includes the steps of introducing the one or more phosphorus sources before or during the growing step and introducing the inoculum of one or more of the deposited strains before or during the growing step. The introduction of the one or more phosphorus sources and the introduction of the inoculum of one or more of the deposited strains may occur at the same time, at substantially the same time, or at different times. In another embodiment the introducing steps may be repeated as necessary.

In one embodiment, the one or more phosphorus sources are rock phosphate.

In another embodiment, the one or more phosphorus sources are fertilizers comprising one or more phosphorus sources. Commercially available manufactured phosphate fertilizers are of many types. Some common ones are those containing rock phosphate, monoammonium phosphate, diammonium phosphate, monocalcium phosphate, super phosphate, triple super phosphate, and/or ammonium polyphosphate. All of these fertilizers are produced by chemical processing of insoluble natural rock phosphates in large scale fertilizer-manufacturing facilities and the product is expensive. By means of the present invention it is possible to reduce the amount of these fertilizers applied to the soil while still maintaining the same amount of phosphorus uptake from the soil.

In still another embodiment, the one or more phosphorus sources are organic phosphorus sources. In a further particular embodiment the source or phosphorus is an organic fertilizer. An organic fertilizer refers to a soil amendment derived from natural sources that guarantees, at least, the minimum percentages of nitrogen, phosphate, and potash. Non-limiting examples of organic fertilizers include plant and animal by-products, rock powders, seaweed, inoculants, and conditioners. These are often available at garden centers and through horticultural supply companies. In particular the organic source of phosphorus is from bone meal, meat meal, animal manure, compost, sewage sludge, or guano, or combinations thereof.

In still another embodiment, the one or more phosphorus sources may be a combination of phosphorus sources including, but not limited to, rock phosphate, monoammonium phosphate, diammonium phosphate, monocalcium phosphate, super phosphate, triple super phosphate, ammonium polyphosphate, fertilizers comprising one or more phosphorus sources, one or more organic phosphorus sources, and combinations thereof.

The methods described herein are potentially useful for improving growth conditions resulting in increased phosphorus uptake and/or yield for any type of plant. In one particular embodiment the plant is selected from the group consisting of non-legumes, legumes, *Brassica* spp., cereals, fruits, vegetables, nuts, flowers, and turf. Particularly the cereals are wheat, corn, rice, oat, rye, barley. Particularly legumes are lentil, chickpeas, beans, soybeans, peas, and alfalfa.

In another particular embodiment the plants are selected from the group consisting of alfalfa, rice, wheat, barley, rye, oat, cotton, sunflower, peanut, corn, potato, sweet potato, bean, pea, chickpeas, lentil, chicory, lettuce, endive, cabbage, brussel sprout, beet, parsnip, turnip, cauliflower, broccoli, turnip, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, sorghum, and sugarcane.

Seed Coatings

In another aspect, seeds are coated with one or more fungal strains selected from the group consisting of:
  the strain having the deposit accession number NRRL B-50776,
  the strain having the deposit accession number NRRL B-50777,
  the strain having the deposit accession number NRRL B-50778,
  the strain having the deposit accession number NRRL B-50779,
  the strain having the deposit accession number NRRL B-50780,
  the strain having the deposit accession number NRRL B-50781,
  the strain having the deposit accession number NRRL B-50782,
  the strain having the deposit accession number NRRL B-50783,
  the strain having the deposit accession number NRRL B-50784,
  the strain having the deposit accession number NRRL B-50785,
  the strain having the deposit accession number NRRL B-50786,
  the strain having the deposit accession number NRRL B-50787,
  the strain having the deposit accession number NRRL B-50788, and
  a mixture of two or more of the strains thereof.

In a particular embodiment, the seed(s) is coated with one or more of the above mentioned deposited strains (e.g., including at least two of the above strains, at least three of the above strains, at least four of the above strains, at least five of the above strains, at least six of the above strains, at least seven of the above strains, at least eight of the above strains, at least nine of the above strains, at least ten of the above strains, at least eleven of the above strains, at least twelve of the above strains, up to and including all of the above strains).

In an embodiment, the seed(s) is coated with the strain having the deposit accession number NRRL B-50776. In an embodiment, the seed(s) is coated with the strain having the deposit accession number NRRL B-50777. In an embodiment, the seed(s) is coated with the strain having the deposit accession number NRRL B-50778. In an embodiment, the seed(s) is coated with the strain having the deposit accession number NRRL B-50779. In an embodiment, the seed(s) is coated with the strain having the deposit accession number NRRL B-50780. In an embodiment, the seed(s) is coated with the strain having the deposit accession number NRRL B-50781. In an embodiment, the seed(s) is coated with the strain having the deposit accession number NRRL B-50782. In an embodiment, the seed(s) is coated with the strain having the deposit accession number NRRL B-50783. In an embodiment, the seed(s) is coated with the strain having the deposit accession number NRRL B-50784. In an embodiment, the seed(s) is coated with the strain having the deposit accession number NRRL B-50785. In an embodiment, the seed(s) is coated with the strain having the deposit accession number NRRL B-50786. In an embodiment, the seed(s) is coated with the strain having the deposit accession number NRRL B-50787. In an embodiment, the seed(s) is coated with the strain having the deposit accession number NRRL B-50788.

In one embodiment, seeds may be treated with composition(s) described herein in several ways but preferably via spraying or dripping. Spray and drip treatment may be conducted by formulating compositions described herein and spraying or dripping the composition(s) onto a seed(s) via a continuous treating system (which is calibrated to apply treatment at a predefined rate in proportion to the continuous flow of seed), such as a drum-type of treater. Batch systems, in which a predetermined batch size of seed and composition(s) as described herein are delivered into a mixer, may also be employed. Systems and apparati for performing these processes are commercially available from numerous suppliers, e.g., Bayer CropScience (Gustafson).

In another embodiment, the treatment entails coating seeds. One such process involves coating the inside wall of a round container with the composition(s) described herein, adding seeds, then rotating the container to cause the seeds to contact the wall and the composition(s), a process known in the art as "container coating". Seeds can be coated by combinations of coating methods. Soaking typically entails using liquid forms of the compositions described. For example, seeds can be soaked for about 1 minute to about 24 hours (e.g., for at least 1 min, 5 min, 10 min, 20 min, 40 min, 80 min, 3 hr, 6 hr, 12 hr, 24 hr).

In certain embodiments, a seed(s) coated with one or more of the compositions described herein will comprise $1\times10^1$-$1\times10^8$, more preferably $1\times10^2$-$1\times10^6$ colony forming units of one or more of the deposited fungal strains per seed.

The invention is further defined by the following numbered paragraphs:

1. An isolated fungal strain selected from the group consisting of:
  the strain having the deposit accession number NRRL B-50777,
  the strain having the deposit accession number NRRL B-50778,
  the strain having the deposit accession number NRRL B-50779,
  the strain having the deposit accession number NRRL B-50780,
  the strain having the deposit accession number NRRL B-50781, the strain having the deposit accession number NRRL B-50782,
the strain having the deposit accession number NRRL B-50783,
the strain having the deposit accession number NRRL B-50784,
the strain having the deposit accession number NRRL B-50785,
the strain having the deposit accession number NRRL B-50786,
the strain having the deposit accession number NRRL B-50787,
the strain having the deposit accession number NRRL B-50788, and
a mixture of two or more of the strains thereof.

2. A composition comprising a carrier and one or more of the fungal strains of paragraph 1.

3. The composition of paragraph 2 comprising an inoculum of one or more of the fungal strains of paragraph 1.

4. The composition of any of paragraphs 2-3, wherein the composition further comprises a phosphorus source.

5. The composition of paragraph 4, wherein the phosphorus source is a rock phosphate.

6. The composition of paragraph 4, wherein the phosphorus source is a fertilizer.

7. The composition of paragraph 6, wherein the fertilizer comprises monoammonium phosphate, diammonium phosphate, monocalcium phosphate, super phosphate, triple super phosphate, ammonium polyphosphate, and combinations thereof.

8. The composition of paragraph 4, wherein the phosphorus source is an organic phosphorus source.

9. The composition of paragraph 8, wherein the organic phosphorus source comprises bone meal, meat meal, animal manure, compost, sewage sludge, guano, or combinations thereof.

10. The composition of any of paragraphs 2-9, wherein the composition further comprises one or more plant signal molecules.

11. The composition of paragraph 10, wherein the one or more plant signal molecules is a lipo-chitooligosaccharide (LCO).

12. The composition of paragraph 11, wherein the LCO is synthetic.

13. The composition of paragraph 11, wherein the LCO is recombinant.

14. The composition of paragraph 11, wherein the LCO is naturally occurring.

15. The composition of paragraph 11, wherein the LCO is obtained from a species of *Rhizobia* selected from *Rhizobium* spp., *Bradyrhizobium* spp., *Sinorhizobium* spp., *Azorhizobium* spp., or a combination thereof.

16. The composition of paragraph 11, wherein the LCO is obtained from *Bradyrhizobium japonicum*.

17. The composition of paragraph 11, wherein the LCO is obtained from an arbuscular mycorrhizal fungus.

18. The composition of paragraph 10, wherein the one or more plant signal molecules is a chitinous compound.

19. The composition of paragraph 18, wherein the chitinous compound is a chito-oligomer (CO).

20. The composition of paragraph 19, wherein the CO is synthetic.

21. The composition of paragraph 19, wherein the CO is recombinant.

22. The composition of paragraph 19, wherein the CO is naturally occurring.

23. The composition of paragraph 10, wherein the one or more plant signal molecules is a flavonoid.

24. The composition of paragraph 23, wherein the flavonoid is luteolin, apigenin, tangeritin, quercetin, kaempferol, myricetin, fisetin, isorhamnetin, pachypodol, rhamnazin, hesperetin, naringenin, eriodictyol, homoeriodictyol, taxifolin, dihydroquercetin, dihydrokaempferol, genistein, daidzein, glycitein, catechin, gallocatechin, catechin 3-gallate, gallocatechin 3-gallate, epicatechin, epigallocatechin, epicatechin 3-gallate, epigallocatechin 3-gallate, cyaniding, delphinidin, malvidin, pelargonidin, peonidin, petunidin, or a derivative thereof.

25. The composition of paragraph 10, wherein the one or more plant signal molecules is jasmonic acid or a derivative thereof.

26. The composition of paragraph 10, wherein the one or more plant signal molecules is linoleic acid or a derivative thereof.

27. The composition of paragraph 10, wherein the one or more plant signal molecules is linolenic acid or a derivative thereof.

28. The composition of paragraph 10, wherein the one or more plant signal molecules is a karrikin.

29. The composition of any of paragraphs 2-28, wherein the carrier is a soil-compatible carrier.

30. The composition of any of paragraphs 2-29, wherein the carrier comprises talc, clay, kaolin, silica gel, starch, cellulose, methylcellulose, polyvinylpyrrolidone, peat, straw, wheat, bran, gum arabic, or combinations thereof.

31. The composition of any of paragraphs 2-30, wherein the carrier is a liquid medium.

32. The composition of any of paragraphs 2-31, wherein the composition further comprises one or more micronutrients.

33. The composition of paragraph 32, wherein the one or more micronutrients comprise copper, iron, zinc, or a combination thereof.

34. A method of increasing the availability of phosphorus for plant uptake from soil, comprising introducing into the soil one or more fungal strains of paragraph 1.

35. The method of paragraph 34, wherein the method comprises introducing into the soil an effective amount of the one or more fungal strains of paragraph 1.

36. The method of paragraph 34, wherein the method comprises introducing an inoculum of the one or more fungal strains of paragraph 1.

37. The method of paragraph 36, wherein the method comprises introducing into the soil an effective amount of the inoculum of the one or more fungal strains of paragraph 1.

38. The method of any of paragraphs 34-37, wherein the method comprises contacting the one or more fungal strains of paragraph 1 with a source of phosphorus.

39. The method of any of paragraphs 34-38, wherein the method further comprises adding a source of phosphorus to the soil.

40. The method of paragraph 39, wherein the phosphorus source is a rock phosphate.

41. The method of paragraph 39, wherein the phosphorus source is a fertilizer.

42. The method of paragraph 41, wherein the fertilizer comprises monoammonium phosphate, diammonium phosphate, monocalcium phosphate, super phosphate, triple super phosphate, ammonium polyphosphate, and combinations thereof.

43. The method of paragraph 39, wherein the phosphorus source is an organic phosphorus source.

44. The method of paragraph 43, wherein the organic phosphorus source comprises bone meal, meat meal, animal manure, compost, sewage sludge, guano, or combinations thereof.

45. The method of paragraph 39, wherein the step of adding a source of phosphorus to the soil occurs before, after, or during the step of introducing into the soil the inoculum of the one or more fungal strains of paragraph 1.

46. The method of any of paragraphs 34-35, wherein the step of introducing into the soil the one or more fungal strains of paragraph 1 comprises introducing the one or more fungal strains of paragraph 1 into the soil in an amount of $1\times10^1$-$1\times10^8$, more preferably $1\times10^6$-$1\times10^{12}$ colony forming units per hectare.

47. The method of any of paragraphs 34-35, wherein the step of introducing into the soil the one or more fungal strains of paragraph 1 comprises introducing the one or more fungal strains of paragraph 1 as a seed coating.

48. The method of paragraph 47, wherein the seed coating comprises $1\times10^1$-$1\times10^8$, more preferably $1\times10^2$-$1\times10^6$ colony forming units per seed.

49. The method of any of paragraphs 36-37, wherein the step of introducing into the soil the inoculum of the one or more fungal strains of paragraph 1 comprises introducing the inoculum into the soil in an amount of $1\times10^1$-$1\times10^8$, more preferably $1\times10^6$-$1\times10^{12}$ colony forming units per hectare.

50. The method of any of paragraphs 36-37, wherein the step of introducing into the soil the inoculum of the one or more fungal strains of paragraph 1 comprises introducing the inoculum as a seed coating.

51. The method of paragraph 50, wherein the seed coating comprises $1\times10^1$-$1\times10^8$, more preferably $1\times10^2$-$1\times10^6$ colony forming units per seed.

52. The method of paragraph 34, comprising introducing into the soil any of the compositions of paragraphs 2-33.

53. A method of increasing the phosphorus uptake in plants comprising growing the plants in a soil comprising a phosphorus source and one or more fungal strains of paragraph 1.

54. The method of paragraph 53, wherein the phosphorus source is a rock phosphate.

55. The method of paragraph 56, wherein the phosphorus source is a fertilizer.

56. The method of paragraph 55, wherein the fertilizer comprises monoammonium phosphate, diammonium phosphate, monocalcium phosphate, super phosphate, triple super phosphate, ammonium polyphosphate, and combinations thereof.

57. The method of paragraph 53, wherein the phosphorus source is an organic phosphorus source.

58. The method of paragraph 57, wherein the organic phosphorus source comprises bone meal, meat meal, animal manure, compost, sewage sludge, guano, or combinations thereof.

59. The method of paragraph 53, wherein the step of adding a source of phosphorus to the soil occurs before, after, or during the step of introducing into the soil an inoculum of the one or more fungal strains of paragraph 1.

60. The method of paragraph 53, wherein the plants are legume plants.

61. The method of paragraph 60, wherein the legume plants are selected from the group consisting of soy bean, bean, alfalfa, and clover.

62. The method of paragraph 53, wherein the plants are non-legume plants.

63. The method of paragraph 62, wherein the non-legume plant is corn.

64. A seed coated with one or more fungal strains of paragraph 1.

65. A seed coated with any of the compositions of paragraphs 2-33.

EXAMPLES

The following examples are provided for illustrative purposes and are not intended to limit the scope of the invention as claimed herein. Any variations in the exemplified examples which occur to the skilled artisan are intended to fall within the scope of the present invention.

Materials & Methods

Deposit of Biological Material

The following biological material has been deposited under the terms of the Budapest Treaty at the Agricultural Research Service Culture Collection, 1815 North University Street, Peoria, Ill. 61604, U.S.A., and given the following accession numbers:

| Identification | Accession Number | Date of Deposit |
| --- | --- | --- |
| Penicillium bilaiae | NRRL B-50776 | 1 Oct. 2012 |
| Penicillium bilaiae | NRRL B-50777 | 1 Oct. 2012 |
| Penicillium bilaiae | NRRL B-50778 | 1 Oct. 2012 |
| Penicillium bilaiae | NRRL B-50779 | 1 Oct. 2012 |
| Penicillium bilaiae | NRRL B-50780 | 1 Oct. 2012 |
| Penicillium bilaiae | NRRL B-50781 | 1 Oct. 2012 |
| Penicillium bilaiae | NRRL B-50782 | 1 Oct. 2012 |
| Penicillium bilaiae | NRRL B-50783 | 1 Oct. 2012 |
| Penicillium bilaiae | NRRL B-50784 | 1 Oct. 2012 |
| Penicillium bilaiae | NRRL B-50785 | 1 Oct. 2012 |
| Penicillium bilaiae | NRRL B-50786 | 1 Oct. 2012 |
| Penicillium bilaiae | NRRL B-50787 | 1 Oct. 2012 |
| Penicillium bilaiae | NRRL B-50788 | 1 Oct. 2012 |

The strain has been deposited under conditions that assure that access to the culture will be available during the pendency of this patent application to one determined by the Commissioner of Patents and Trademarks to be entitled thereto under 37 C.F.R. § 1.14 and 35 U.S.C. § 122. The deposit represents a pure culture of the deposited strain. The deposit is available as required by foreign patent laws in countries wherein counterparts of the subject application or its progeny are filed. However, it should be understood that the availability of a deposit does not constitute a license to practice the subject invention in derogation of patent rights granted by governmental action.

Example 1: Phosphate Solubilization Assays

Fungal growth for phosphate solubilization assays was carried out in 96-well microbioreactor plates (EnzyScreen, Netherlands) in 1.5 ml of nitrate free minimal salts medium (Table 1). The plates were inoculated from glycerol spore suspension stock plates stored at 80° C. using a 96-pin cryo-replicator that was heat sterilized and cooled before transfer. Plates were grown at room temperature (20-25° C.) and 300 rpm for 14 days. After 14 days, the plate was centrifuged for 5 minutes at 5100 rpm and 1 ml of the supernatant was transferred to a 96-well filter plate (Acro-Prep Advance 96 multi-well filter plate, 1 µm glass fibre, Pall Life Sciences #8231). The filter plate was placed over a 2 ml receiver plate (Whatman Uniplate 96well round bottom, Whatman#7701-5200) and samples were filtered under vacuum using a multi-well plate vacuum manifold (Pall Life Sciences #5017). The filtered supernatants were diluted 100× with sterile water and soluble phosphate was measured using a plate reading spectrophotometer (Biotek, Winooski, Vt.) with the BioVision Phosphate Colorimetric Assay Kit (BioVision Research Products, Mountain View, Calif.) and accompanying instructions. Each isolate was grown and tested for phosphate solubilization in triplicate and the average and standard deviations were calculated. Results are provided in Table 2.

TABLE 1

Nitrate Free Minimal salts media (NFMSM)

| Component | g/L |
|---|---|
| NaCl | 0.1 |
| $NH_4Cl$ | 0.4 |
| $CaCl_2 \cdot 2H_2O$ | 0.1 |
| $MgSO_4 \cdot 7H_2O$ | 1.0 |
| sucrose | 10.0 |
| hydroxyapatite | 5.41 |

TABLE 2

Phosphate solubilization from hydroxyapatite by hybrids and their parents. Numbers represent the average ± standard deviation of 3 replicates.

| Isolate | Average $P_2O_5$ solubilized |
|---|---|
| ATCC 20851 (parent) | 883 ± 92 |
| V08/021001 (parent) | 849 ± 52 |
| ATCC 22348 (parent) | 1047 ± 115 |
| NRRL B-50776 | 1174 ± 210 |
| NRRL B-50777 | 1089 ± 95 |
| NRRL B-50778 | 1066 ± 172 |
| NRRL B-50779 | 1108 ± 99 |
| NRRL B-50780 | 892 ± 101 |
| NRRL B-50781 | 870 ± 43 |
| NRRL B-50782 | 1009 ± 100 |
| NRRL B-50783 | 1228 ± 294 |
| NRRL B-50784 | 886 ± 56 |
| NRRL B-50785 | 881 ± 174 |
| NRRL B-50786 | 961 ± 97 |
| NRRL B-50787 | 976 ± 116 |
| NRRL B-50788 | 1085 ± 72 |

Results indicate that all of the isolates solubilized more phosphate than parental strain V08/021001. Results further indicate that 11 of the 13 isolates solubilized more phosphate than parental strain ATCC 20851. 5 isolates solubilized more phosphate than parental strain ATCC 22348.

Example 2: Gluconic Acid Production of Hybrids

Organic acid production is correlated with the ability to solubilize phosphate. Some organic acids, however, can be toxic to plants (J. A. L. van Kan, Trends in Plant Science 11: 247-253 (2006)). Gluconic acid is not toxic to plants and its production by *P. bilaiae* shows strong correlation to phosphate solubilization. Gluconic acid production by 5 of the isolates and their respective parents was studied using high performance liquid chromatography (HPLC). Twenty µl of the supernatant from Example 1 was run through an HPLC column (Restek Allure Organic Acids column (250×4.6 mm, 5 µm)) at 15° C. The mobile phase consisted of 25 mM phosphate buffer (adjusted to pH 2.5 with phosphoric acid) running at 1 ml/min on an Agilent Infinity 1260 HPLC equipped with a diode array detector (DAD). The gluconic acid peak was identified by comparison to a standard of pure gluconic acid. The area under the gluconic acid peak was measured and averaged across three replicate experiments. Results are provided in Table 3.

TABLE 3

Gluconic acid production of 5 hybrids and their parents. Numbers represent the average ± standard deviation of the area under the gluconic acid peak of 3 independent replicates.

| Isolate | Gluconic acid (arbitrary units) |
|---|---|
| ATCC 20851 (parent) | 1984 ± 65 |
| V08/021001 (parent) | 1691 ± 93 |
| ATCC 22348 (parent) | 2252 ± 33 |
| NRRL B-50776 | 2156 ± 60 |
| NRRL B-50777 | 2261 ± 25 |
| NRRL B-50779 | 2252 ± 48 |
| NRRL B-50783 | 2245 ± 58 |
| NRRL B-50788 | 2228 ± 45 |

Results indicate that all of the isolates produced more gluconic acid than at least one parent and 3 out of 5 isolates produced more gluconic acid than either parent.

It will be understood that the Specification and Examples are illustrative of the present embodiments and that other embodiments within the spirit and scope of the claimed embodiments will suggest themselves to those skilled in the art. Although this invention has been described in connection with specific forms and embodiments thereof, it would be appreciated that various modifications other than those discussed above may be resorted to without departing from the spirit or scope of the invention as defined in the appended claims. For example, equivalents may be substituted for those specifically described, and in certain cases, particular applications of steps may be reversed or interposed all without departing from the spirit or scope for the invention as described in the appended claims.

The invention claimed is:

1. A composition comprising a soil-compatible carrier and the *Penicillium bilaiae* strain having the deposit accession number NRRL B-50776.

2. The composition of claim 1, wherein said composition further comprises one or more phosphorous sources.

3. The composition of claim 1, wherein said composition further comprises one or more lipo-chitooligosaccharides and/or chitooligosaccharides.

4. The composition of claim 1, wherein said composition further comprises one or more chitins and/or chitosans.

5. The composition of claim 1, wherein said composition further comprises one or more flavonoids.

6. The composition of claim 1, wherein said composition further comprises one or more diazotrophic microorganisms.

7. The composition of claim 1, wherein said composition further comprises one or more mycorrhizae.

8. The composition of claim 1, wherein said composition further comprises one or more herbicides, fungicides and/or insecticides.

9. A seed treated with the composition of claim 1.

10. The seed of claim 9, wherein said seed is coated with $1 \times 10^1$ to $1 \times 10^8$ colony-forming units of the *Penicillium bilaiae* strain having the deposit accession number NRRL B-50776.

11. A container comprising a plurality of seeds treated with the composition of claim 1.

* * * * *